(12) United States Patent
Gale et al.

(10) Patent No.: US 9,278,485 B2
(45) Date of Patent: *Mar. 8, 2016

(54) METHOD TO PREVENT STENT DAMAGE CAUSED BY LASER CUTTING

(71) Applicant: ABBOTT CARDIOVASCULAR SYSTEMS INC., Santa Clara, CA (US)

(72) Inventors: David C. Gale, Kennesaw, GA (US); Yunbing Wang, Sunnyvale, CA (US); Svava Maria Atladottir, Mountian View, CA (US); Klaus Kleine, Los Gatos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 419 days.

This patent is subject to a terminal disclaimer.

(21) Appl. No.: 13/736,864

(22) Filed: Jan. 8, 2013

(65) Prior Publication Data

US 2013/0119586 A1    May 16, 2013

Related U.S. Application Data

(63) Continuation of application No. 12/554,764, filed on Sep. 4, 2009, now Pat. No. 8,373,090.

(51) Int. Cl.
| | |
|---|---|
| *B29C 71/04* | (2006.01) |
| *B23K 26/38* | (2014.01) |
| *B29C 53/82* | (2006.01) |
| *B29C 33/42* | (2006.01) |
| *B29C 67/00* | (2006.01) |
| *B26D 3/16* | (2006.01) |
| *B29C 59/16* | (2006.01) |

(Continued)

(52) U.S. Cl.
CPC ............. *B29C 71/04* (2013.01); *B23K 26/0823* (2013.01); *B23K 26/38* (2013.01); *B23K 26/402* (2013.01); *B26D 3/164* (2013.01); *B29C 33/42* (2013.01); *B29C 53/82* (2013.01); *B29C 59/165* (2013.01); *B29C 67/0022* (2013.01); *A61F 2/91* (2013.01); *A61F 2240/001* (2013.01); *B23K 2203/42* (2015.10); *B29C 2059/027* (2013.01); *B29C 2791/009* (2013.01); *B29C 2793/0018* (2013.01)

(58) Field of Classification Search
USPC .......................................... 264/156, 162, 400
See application file for complete search history.

(56) References Cited

U.S. PATENT DOCUMENTS

| | | |
|---|---|---|
| 4,674,506 A | 6/1987 | Alcond |
| 5,700,285 A | 12/1997 | Myers et al. |

(Continued)

FOREIGN PATENT DOCUMENTS

| | | |
|---|---|---|
| DE | 199 01 530 | 7/2000 |
| WO | WO 97/18058 | 5/1997 |
| WO | WO 2008/005390 | 1/2008 |

OTHER PUBLICATIONS

U.S. Appl. No. 11/811,982, filed Jun. 12, 2007, Yang.

(Continued)

*Primary Examiner* — Atul P. Khare
(74) *Attorney, Agent, or Firm* — Squire Patton Boggs (US) LLP

(57) ABSTRACT

Apparatus, method and system for cutting a polymeric stent including the use of a polymeric mandrel as a laser shielding device. The polymeric mandrel is allowed to roll freely within a polymeric tube that is cut into a polymeric stent.

13 Claims, 8 Drawing Sheets

(51) Int. Cl.
*B23K 26/08* (2014.01)
*B23K 26/40* (2014.01)
*A61F 2/91* (2013.01)
*B29C 59/02* (2006.01)

(56) References Cited

U.S. PATENT DOCUMENTS

| | | | |
|---|---|---|---|
| 5,759,192 | A | 6/1998 | Saunders |
| 5,780,807 | A | 7/1998 | Saunders |
| 5,906,759 | A | 5/1999 | Richter |
| 5,922,005 | A | 7/1999 | Richter et al. |
| 5,935,506 | A | 8/1999 | Schmitz et al. |
| 6,160,240 | A | 12/2000 | Momma et al. |
| 6,521,865 | B1 * | 2/2003 | Jones et al. ............... 219/121.72 |
| 6,927,359 | B2 * | 8/2005 | Kleine et al. ............. 219/121.72 |
| 7,622,070 | B2 * | 11/2009 | Atladottir et al. ............. 264/400 |
| 2002/0038767 | A1 | 4/2002 | Trozera |
| 2002/0193866 | A1 | 12/2002 | Saunders |
| 2003/0069629 | A1 | 4/2003 | Jadhav et al. |
| 2003/0234242 | A1 | 12/2003 | McCoy |
| 2004/0060508 | A1 | 4/2004 | Pacetti et al. |
| 2004/0168298 | A1 | 9/2004 | Dolan et al. |
| 2004/0226922 | A1 | 11/2004 | Flanagan |
| 2004/0232120 | A1 | 11/2004 | Wessner |
| 2006/0287715 | A1 | 12/2006 | Atladottir et al. |
| 2007/0023974 | A1 | 2/2007 | Wu |
| 2007/0045255 | A1 | 3/2007 | Kleine et al. |
| 2007/0151961 | A1 | 7/2007 | Kleine et al. |
| 2008/0021541 | A1 * | 1/2008 | Saunders ...................... 623/1.15 |
| 2010/0106242 | A1 | 4/2010 | Ozkan et al. |

OTHER PUBLICATIONS

U.S. Appl. No. 12/259,114, filed Oct. 27, 2008, Ozkan.
International Search Rep. For PCT/US2007/015777 filed Jul. 10, 2007, mailed Dec. 4, 2007, 6 pgs.
International Search Report for PCT/US2006/020883 filed May 26, 2006, mailed Sep. 11, 2007, 12 pgs.
Perry et al., "Ultrashort-pulse laser machining", Section K-ICALEO pp. 1-20 (1998).
"Femtosecond Lasers", Encyclopedia of Laser Physics and Technology, downloaded from www.rp-photonics.com/fetosecond_lasers.html, Apr. 14, 2008, 4 pgs.

* cited by examiner

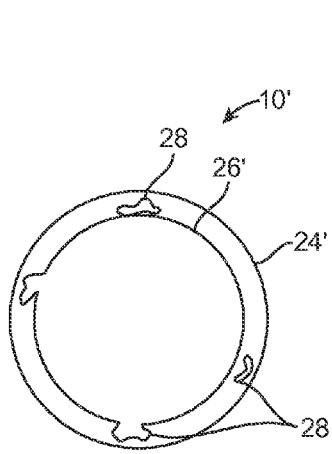
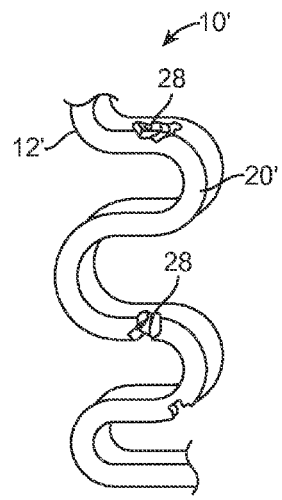
FIG. 3 (PRIOR ART)  FIG. 4 (PRIOR ART)
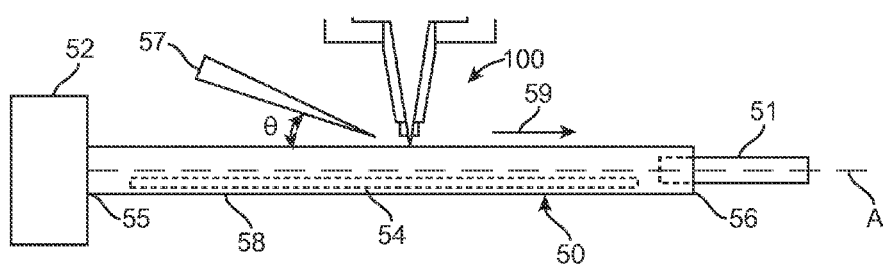
FIG. 5

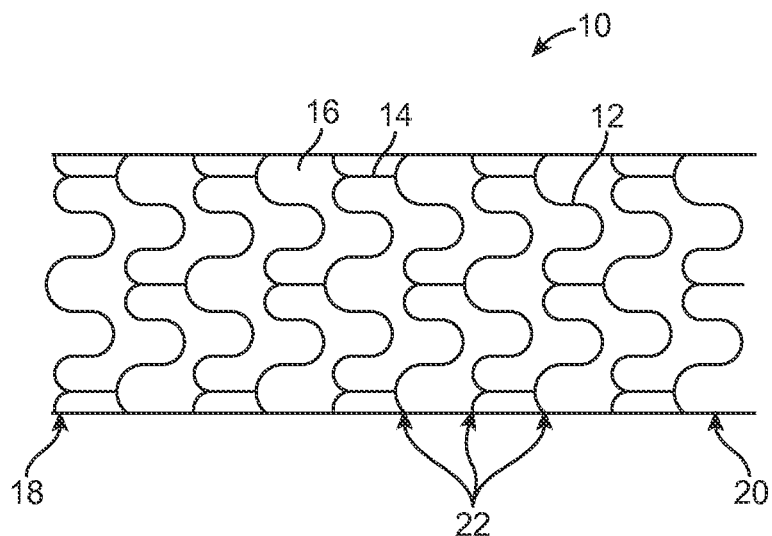
FIG. 9
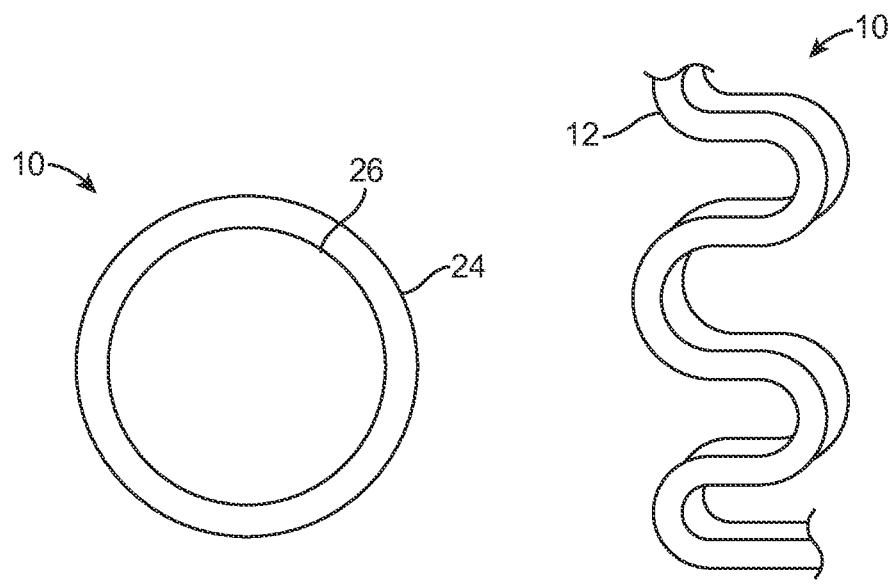
FIG. 10
FIG. 11

METHOD TO PREVENT STENT DAMAGE CAUSED BY LASER CUTTING

CROSS REFERENCE TO RELATED APPLICATION

This application is a continuation of application Ser. No. 12/554,764, which is incorporated by reference herein, which was filed on Sep. 4, 2009.

BACKGROUND OF THE INVENTION

1. Field of the Invention

The present invention relates to stents; more particularly, this invention relates to processes for making a polymer-based stent.

2. Background of the Invention

The invention relates to radially expandable endoprostheses which are adapted to be implanted in a lumen of a tubular organ. An "endoprosthesis", or stent, corresponds to an artificial implantable medical device that is placed inside the body. A "lumen" refers to a cavity of a tubular organ such as a blood vessel. A stent is an example of these endoprostheses. Stents are generally cylindrically shaped devices which function to hold open and sometimes expand a segment of a blood vessel or other anatomical lumens such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

A treatment involving a stent includes both delivery and deployment of the stent. "Delivery" refers to introducing and transporting the stent through a lumen of a tubular organ to a region requiring treatment. "Deployment" corresponds to the expanding of the stent within the lumen at the treatment region. Delivery and deployment of a stent may be accomplished by positioning the stent about one end of a catheter, inserting the end of the catheter through the skin into the lumen, advancing the catheter in the lumen to a desired treatment location, expanding the stent at the treatment location, and then removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

Stents have been made of many materials including metals and polymers. Polymer materials include both nonbioerodable and bioerodable plastic materials. In some applications, a polymeric bioerodable stent may be more advantageous than a metal stent due to its biodegradeability and increased flexibility relative to the metal stent. The cylindrical structure of a stent is typically composed of a scaffolding that includes a pattern or network of interconnecting structural elements or struts. The scaffolding can be formed from wires, tubes, or planar films of material rolled into a cylindrical shape. In addition, a medicated stent may be fabricated by coating the surface of either a metallic or polymeric scaffolding with a polymeric carrier. The polymeric carrier can include an active agent or drug. Furthermore, the pattern that makes up the stent allows the stent to be radially expandable and longitudinally flexible. Longitudinal flexibility facilitates delivery of the stent and rigidity is needed to hold open a lumen of a tubular organ. Generally, the pattern should be designed to maintain the longitudinal flexibility and rigidity required of the stent. The stent should also have adequate strength in the circumferential direction.

A number of techniques have been suggested for the fabrication of stents from tubes and planar films or sheets. One such technique involves laser cutting or etching a pattern onto a material. Laser cutting may be performed on a planar film of a material which is then rolled into a tube. Alternatively, a desired pattern may be etched directly onto a tube. Other techniques involve cutting a desired pattern into a sheet or a tube via chemical etching or electrical discharge machining. Laser cutting of stents has been described in a number of publications including U.S. Pat. No. 5,780,807 to Saunders, U.S. Pat. No. 5,922,005 to Richter and U.S. Pat. No. 5,906,759 to Richter.

In a typical method of manufacturing a metal stent with a laser, a mandrel is placed inside the lumen of metal tubing. A "mandrel" refers to a metal bar or rod on which an implantable medical device may be shaped. The mandrel provides structural support to the tubing as it is being cut and shaped. See, e.g., U.S. Pat. No. 5,780,807 to Saunders. After a stent has been cut, the support on at least one end must be removed to allow removal of the stent. A new piece of tubing is then attached and must be realigned and re-supported. Therefore, there is a need for a stent cutting device that allows removal of completed stents from the apparatus and allows for the cutting of more stents from the remaining tubing without the inherent inefficiencies of readjusting the support means for the removal of each stent.

SUMMARY OF THE INVENTION

The invention is directed to methods, systems, and apparatuses for manufacturing polymeric stents.

One aspect of the present invention is directed to a method of producing a polymeric stent, comprising: positioning a polymeric mandrel and polymeric tube relative to the other such that the polymeric mandrel is within the polymeric tube and in contact with the polymeric tube inside surface, forming a tubing-mandrel assembly, wherein the polymeric tube has a first end and a second end; cutting the polymeric tube while the polymeric mandrel is positioned within the polymeric tube with a laser to form a stent, wherein during the cutting the polymeric tube rotates and the polymeric mandrel rolls in response to an angular force from the rotation of the polymeric tube, wherein the polymeric mandrel rolls on the inside surface of the polymeric tube; and removing the stent from the mandrel.

Another aspect of the present invention is directed to a stent cutting apparatus, comprising: a generally tubular polymeric member having a working outer tube and an inner tube surface defining an inside diameter of the generally tubular polymeric member, the generally tubular polymeric member having a first end and a second end; a polymeric mandrel having an outer surface defining an outer diameter that is smaller than the inside diameter of the generally tubular polymeric member; a support adapted to hold the generally tubular polymeric member only at the first end, with the polymeric mandrel therewithin, in operative association with a laser beam; and a nozzle near the laser beam cutting point adapted to dispense pressurized gas, thereby forming a jet of pressurized gas to force debris out of the laser cut kerf toward the second end of the generally tubular polymeric member, wherein the polymeric mandrel is positioned longitudinally within the generally tubular polymeric member such that the outer surface of the polymeric mandrel is in contact with the inner tube surface of the generally tubular polymeric member.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIG. 3 is a cross-sectional view of a polymeric stent of FIG. 2 manufactured using inadequate protection from the laser cutter.

FIG. 4 is an enlarged view of a portion of a distal ring of the polymeric stent of FIG. 2 manufactured using inadequate protection from the laser cutter.

FIG. 5 illustrates an embodiment of a polymeric stent manufacturing device used in one form of a method of the present invention.

FIG. 9 shows an enlarged view of a polymeric stent manufactured by the stent manufacturing device of the present invention.

FIG. 10 is a cross-sectional view of the polymeric stent of FIG. 9.

FIG. 11 is an enlarged view of a portion of a distal ring of the polymeric stent of FIG. 9.

DETAILED DESCRIPTION OF EMBODIMENTS

In a conventional lasing process of manufacturing a polymeric stent from a tube, a mandrel may not typically be employed. Due to the retentive nature of polymeric materials for foreign particulates, a glass or metal mandrel may contaminate the polymeric stent if a laser beam from the laser strikes it and releases such contaminates. The glass or metal debris can not be cleaned from the surface of the polymer stent using conventional techniques commonly employed for metal stents, such as electropolishing due to the sensitivity of the polymer stent to aggressive chemicals and heat treatments. In other words, a glass mandrel may leave glass particulates, and a metal mandrel may leave large amounts of metal oxide contamination melted into the inner surface of the polymer stent, respectively. Such contaminants may cause adverse effects during and/or after the stent is implanted into the lumen of a bodily organ, including the increased mortality rate of mammals during preclinical trials due to glass contamination. The increased mortality is due to the thrombus formation caused by the interaction of blood with the glass debris. The glass debris causes a very strong thrombotic response, which may lead to vessel occlusion and death.

However, non-use of a mandrel in the manufacturing process of a polymeric stent, may cause problems aside from contamination through use of glass or metal mandrels. It has been observed that in the manufacture of polymeric stents, damage to the inner surface of the stent can occur. The damage is typically in the form of at least one angled cut, or "nick", within the inner surface area. The angled cuts are the result of the laser beam reaching the inner surface as the equal-but-opposite outer surface is being lased. The damage caused thereby may cause problems with delivery of the stent and/or adverse body reactions. This problem may be remedied by use of a typical mandrel (which may provide a shielding effect) in the manufacturing process; however, the problems associated with the use of metal or glass mandrels as described previously may result. Additional damage that is not readily apparent may also be caused. The impact of an unfocused laser beam on the opposite side of the tube may cause molecular weight loss that is not readily detectible. This may result in a change in the mechanical properties of the stent in an unpredictable manner.

Figure 1:
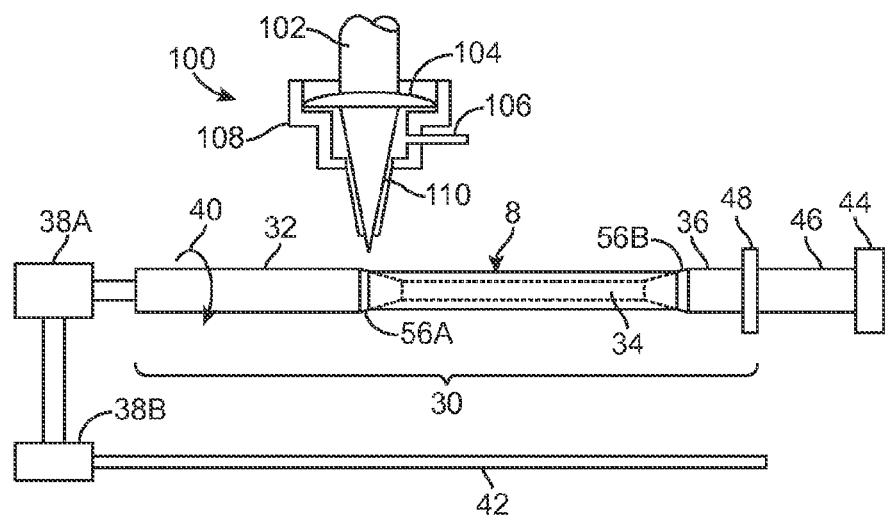
FIG. 1 illustrates a polymeric stent manufacturing device used in one form of a method for manufacturing a polymeric stent.

FIG. 1 illustrates a polymeric stent manufacturing device 30 related to the manufacturing process of a polymeric stent. Device 30 for supporting a polymeric tube 8 includes a support member 32 and a lock member 36. Support member 32 may connect to a motor 38A to provide rotational motion about the longitudinal axis of a stent (depicted by arrow 40). Another motor 38B may also be provided for moving device 30 in a back and forth linear direction along rail 42. Polymeric stent manufacturing device 30 may be in fluid communication with a vacuum device 44 for collecting excess polymeric material. Lock member 36 may be coupled to the vacuum device 44 via a conduit 46. A coupler 48 allows device 30 to rotate with respect to conduit 46 and vacuum 44. A mandrel 34 is attached between support member 32 and lock member 36. The outer diameter of mandrel 34 will typically be smaller than the inner diameter of polymeric tube 8, as positioned on fixture 30, so as to prevent the outer surface of mandrel 34 from making contact with the inner surface of polymeric tube 8. Support member 32 and lock member 36 include conical end portions 56A and 56B, instead of flat ends, for penetrating into ends of polymeric tube 8. The end portions 56A and 56B can taper inwardly at an angle of about 15 degrees to about 75 degrees, more narrowly from about 30 degrees to about 60 degrees. By way of example, angle θ can be about 45 degrees. If the outer diameter of the mandrel is in contact with the inner diameter of the tube from which the stent is cut then there is a very strong probability that the inner mandrel will be welded to the stent.

Figure 2:
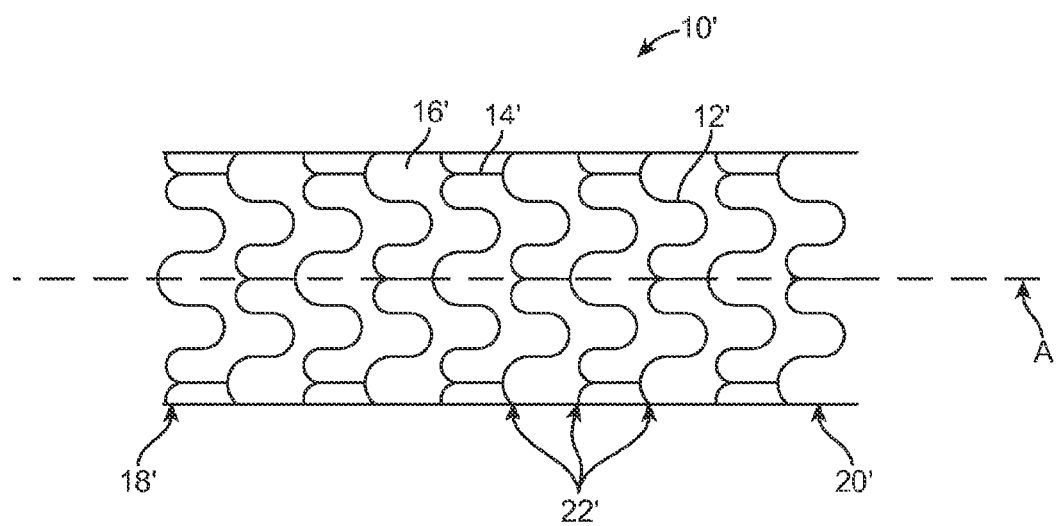
FIG. 2 shows an enlarged view of a polymeric stent manufactured by the stent manufacturing device in FIG. 1.

In the manufacturing process, a polymeric tube 8 may be placed over the mandrel 34 between support member 32 and lock member 36. The wall thickness of the polymeric tube 8 will typically vary throughout the tube body due to variations in the manufacturing process of polymeric tubes. A coaxial gas jet, rotary collet, tube support and beaming block apparatus of a laser (from hereonout abbreviated as a laser 100) may then be used for the etching process to form a polymeric stent 10' from the polymeric tube 8. The laser 100 can include a laser beam 102, a focusing lens 104, a gas input 106, a coaxial gas jet assay 108 and a gas jet 110. A resultant polymeric stent 10' manufactured using device 30 is illustrated in FIG. 2. Polymeric stent 10' includes a plurality of struts 12' linked by connecting elements 14' with gaps 16' positioned in between struts 12' and connecting elements 14'. The polymeric stent 10' can include a proximal ring 18', a distal ring 20' and at least one central ring 22'.

FIG. 3 is a cross-section of the polymeric stent 10' of FIG. 2 if it is manufactured without using a protective mandrel or with a mandrel of incorrect thickness. As shown, the stent 10' includes an inner surface 26' and an outer surface 24'. The inner surface 26' of the stent 10' may have at least one "nick" or angled cut 28 when manufactured using the device 30 without an adequate mandrel. In FIG. 4, an enlarged view of a portion of the distal ring 20' is depicted. In this view, at least one angled cut 28 on the inner surface 26' can be seen more clearly. It should be understood that the angled cuts 28 may occur throughout the inner surface 26' of the stent 10'.

The manufacturing process as discussed in connection with FIG. 1 has several drawbacks. First, the process may lead to the manifestation of angled cuts 28. For example, if the mandrel is too thick, the laser power may be diverted to a different portion of the polymeric tube 8, contributing to the manifestation of angled cuts 28. After the laser enters the polymeric tube 8, its power decreases as it gets further from the surface. If the beam encounters a mandrel soon after entering the polymeric tube 8, then the energy may not have dissipated very much and the beam may be deflected to a nearer inner surface with more energy, thereby contributing to angled cuts 28. In addition, the inherent varying wall thickness of the polymeric tubes may contribute to the manifestation of angled cuts 28. As an illustration, the power of the laser 100 may be adjusted to etch a first portion of the polymeric tube 8 with a first thickness. However, this same power may be too strong for the etching of a second portion of polymeric tube 8 with a second thickness. As a result, although appropriate for the first portion of polymeric tube 8 with the first thickness, the same power of the laser 100 for the second portion of the polymer tube 8 with the second thickness may be too strong and therefore cause the manifestation of angled cuts 28. The typical wall thickness of a tube from which a stent is cut is 0.006"+/−0.001", which may lead to the variation discussed above.

A second drawback to the manufacturing process in FIG. 1 is a resulting rough inner surface of polymeric tube 8 due to the inability to clear away debris from the cutting area. This may result in heat buildup that is undesired in certain areas of the stent. Additionally, rough surfaces can cause an increase in protein accumulation leading to a thrombogenic response. The present invention solves the problem by polishing the inside surface of polymeric tube 8 while the tube is being cut into a stent.

A third drawback to the manufacturing process in FIG. 1 is the inability to cut more than one stent without having to move and reposition support member 32 and lock member 36 for each new stent.

In FIGS. 5 through 9, embodiments of a polymeric stent manufacturing device 50, 70, 80 related to a manufacturing process of the present invention are illustrated. In FIG. 5, device 50 for supporting a polymeric tube 58 can include a first support member 52 at first end 55 of polymeric tube 58, a polymeric mandrel 54, and a second support member 51 at the second end 56 of polymeric tube 58. Support member 52 may contain a motor to provide rotational motion about the longitudinal axis A of a stent. The types and specifications of the various motors which can be used in any of the embodiments herein would be apparent to those skilled in the art. The term stent is broadly intended to include self- and balloon-type as well stent-grafts.

Polymeric mandrel 54 is allowed to freely roll around the inside diameter of polymeric tube 58. In some embodiments, polymeric mandrel 54 is not supported specifically at either end, but supported along its entire length by polymeric tube 58. Polymeric mandrel 54 may be hollow or solid and made from the same or different polymer(s) as polymeric tube 58. In an embodiment as shown in FIG. 6B, polymeric mandrel 64 with an outside diameter of $OD_M$ is positioned longitudinally within polymeric tube 68 of inside diameter $ID_T$ such that it is in contact with approximately the bottom of polymeric tube 68. As polymeric tube 68 is rotated in direction $D_T$, polymeric mandrel will roll in direction $D_M$. Freely roll is understood to mean the travel of polymeric mandrel 64 in reaction to the angular force applied by rolling polymeric tube 68. In an embodiment, friction F at the contact point between polymeric mandrel 64 and polymer tube 68, and gravity G are the major external forces applied to polymeric mandrel 64. If friction F is not too high, polymeric mandrel 64 will smoothly roll to a new position near the bottom of polymeric tube 68. If friction F is high, or there are imperfections like bumps on the inside surface of polymeric tube 68, or on the surface of polymeric mandrel 64, then polymeric mandrel 64 may have a bouncy, irregular, motion. Friction F may be increased by roughening the surface of polymeric mandrel 64 or roughening the inside surface of polymeric tube 68. In an embodiment, polishing of the inside surface of polymeric tube 68 may occur using a rough polymeric mandrel 64. In another embodiment, a smooth polymeric mandrel 64 may be used to polish the inner surface of polymeric tube 68.

Polymeric stent manufacturing device 50 is positioned under a laser cutter 100 for cutting polymeric tube 58. An optional nozzle 57 provides pressurized gas to the surface of polymeric tube 58 near the laser cutting site. Nozzle 57 is positioned relative to the outside surface of polymeric tube 58 at an angle θ of about 15 degrees to about 75 degrees, more narrowly from about 30 degrees to about 60 degrees. By way of example, angle θ can be about 45 degrees.

The pressurized gas can be any gas including air or inert gases such as nitrogen, helium, and argon. In an embodiment the gas is helium. The gas aids in forcing debris out of a laser cut kerf in direction 59 toward the second end of polymeric tube 58. In another embodiment, the gas is cool, facilitating in cooling the generally tubular polymeric tube 58 and/or polymeric mandrel 54. In some embodiments, the gas temperature is ambient, less than ambient, or greater than ambient. In one embodiment the pressurized gas temperature is supplied between about 0° C. and about 25° C. The flowrate of the gas may range from about 2 SCFH to about 10 SCFH. The assist gas will also influence the nature of the plasma formed during the cutting process.

Figure 6A:
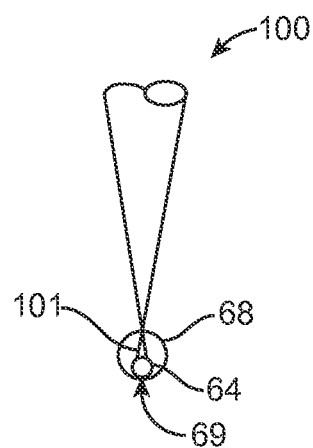
FIG. 6A is an end view of the embodiment of the device in FIG. 5.
Figure 6B:
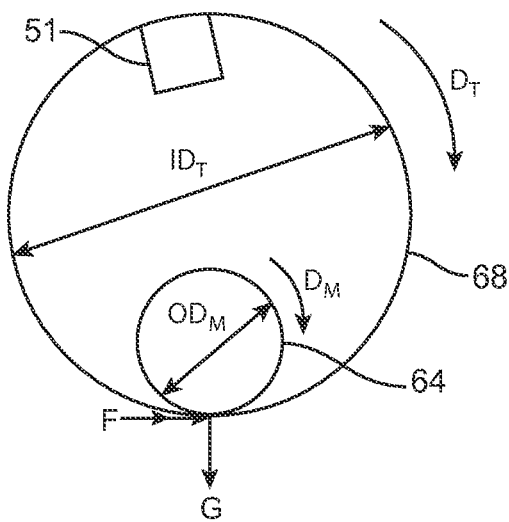
FIG. 6B is a radial view of the polymeric stent and polymeric mandrel of the present invention.

FIG. 6A is a cross-sectional end view of the apparatus in FIG. 5 showing polymeric tube 68 with polymeric mandrel 64 protecting the inside surface of polymeric tube 68 opposite laser 100 from the cutting beam. Beam 101 passes through a space between the inner tube surface of generally tubular polymeric member 68 and the outer surface of polymeric mandrel 64 and contacts polymeric mandrel 64 such that the laser beam is prevented from contacting the portion of the inner tube surface 69 upon which polymeric mandrel 64 is placed.

Figure 7A:
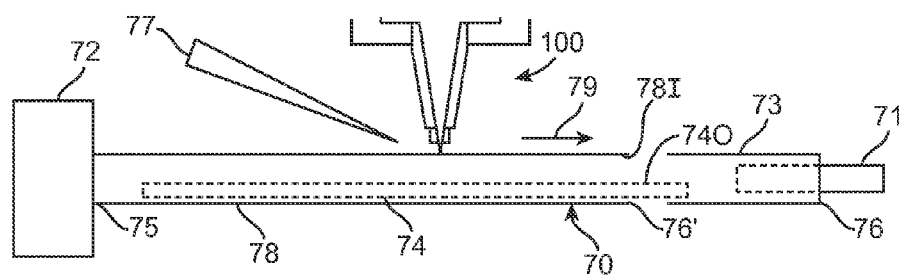
FIG. 7A illustrates an embodiment of a polymeric stent manufacturing device used in the present invention.
Figure 7B:
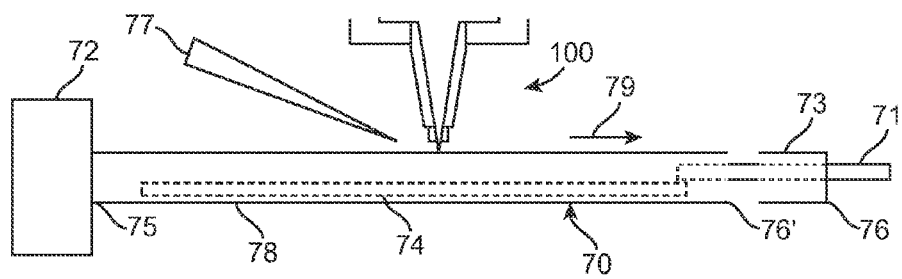
FIG. 7B illustrates another embodiment of a polymeric stent manufacturing device used in the present invention.
Figure 7C:
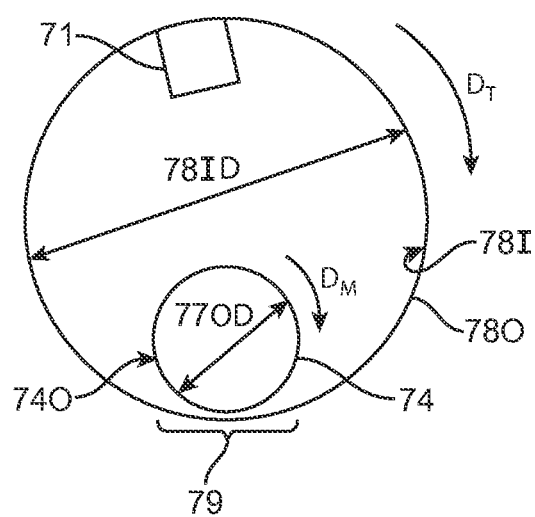
FIG. 7C illustrates an end view of the embodiment of the device in FIGS. 7A, 7B.

FIGS. 7A, 7B and 7C illustrate several embodiments of the apparatuses and methods for cutting a stent according to the present invention. A generally tubular polymeric member 78 having a working outer tube 78 O and an inner tube surface 78 I defining an inside diameter 78 ID and having a first end 75 and a second end 76, has its first end 75 mounted on support 72 and its second end 76 mounted on second support 71. A polymeric mandrel 74 having an outer surface 74 O defining an outer diameter 74 OD that is smaller than the inside diameter of generally tubular polymeric member 78 is placed within generally tubular polymeric member 78. Apparatus 70 is placed in operative association with laser beam 100 which impinges upon the working outer tube surface thereby causing the laser beam 100 to cut a kerf. The beam then passes through a space between the inner tube surface 78 I of generally tubular polymeric member 78 and the outer surface 74 O of polymeric mandrel 74 and contacts polymeric mandrel 74 such that the laser beam 100 is prevented from contacting the area of the inner tube surface 79 upon which polymeric mandrel 74 is placed and shields. Optionally, pressurized gas is dispensed through a nozzle 77 near the laser beam cutting point, thereby forming a jet of pressurized gas to force debris out of the laser cut kerf in direction 79 toward the second end 76 of generally tubular polymeric member 78. A stent pattern is cut in generally tubular polymeric member 78 near the second end 76 and the completed stent 73 is removed from the second end 76 of generally tubular polymeric member 78 by sliding stent 73 onto second support 71. In FIG. 7A, the new second end 76' of generally tubular polymeric member 78 is not supported by second support 71 after the first stent 73 has been removed. A second stent may now be cut from the remaining portion of generally tubular polymeric member 78 near new second end 76'.

In one embodiment as illustrated in FIG. 7B, generally tubular polymeric member 78 may continue to be supported at the new second end 76' by second support 71 after the first stent 73 has been removed. This may be accomplished by moving second support 71 into the new second end 76' of the remaining portion of generally tubular polymeric member 78 while stent 73 is still on second support 71. Polymeric mandrel 74 may also be moved toward support 72 to accommodate second support 71.

Figure 8A:
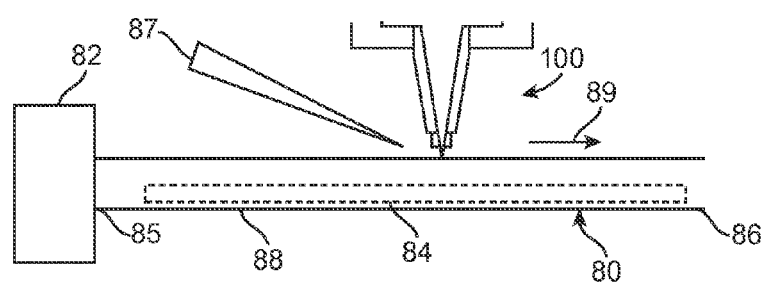
FIG. 8A illustrates a further embodiment of a polymeric stent manufacturing device used in the present invention.
Figure 8B:
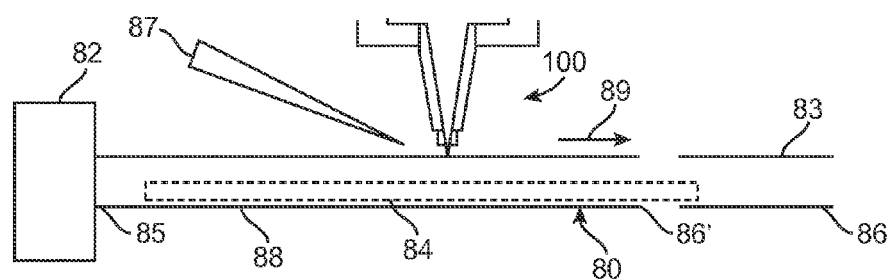
FIG. 8B illustrates an embodiment of a polymeric stent manufacturing device used in the present invention.
Figure 8C:
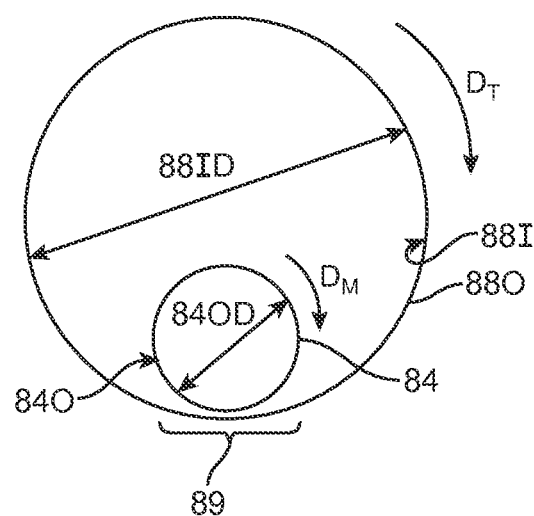
FIG. 8C illustrates an end view of an embodiment of the device in FIGS. 8A, 8B.

FIGS. 8A and 8B illustrate several embodiments of the apparatuses and methods for cutting a stent according to the present invention. A generally tubular polymeric member 88 having a working outer tube 88 O and an inner tube surface 88 I defining an inside diameter 88 ID and having a first end 85 and second end 86, has its first end 85 mounted on support 82 and its second end 86 left unsupported. A polymeric mandrel 84 having an outer surface 84 O defining an outer diameter 84 OD that is smaller than the inside diameter 88 ID of generally tubular polymeric member 88 is placed within generally tubular polymeric member 88. Apparatus 80 is placed in operative association with laser beam 100 which impinges upon the working outer tube surface thereby causing the laser beam 100 to cut a kerf. The beam then passes through a space between the inner tube surface 88 I of generally tubular polymeric member 88 and the outer surface 84 O of polymeric mandrel 84 and contacts polymeric mandrel 84 such that the laser beam 100 is prevented from contacting the area of the inner tube surface 89 upon which polymeric mandrel 84 is placed and shields. Pressurized gas is dispensed through a nozzle 87 near the laser beam cutting point, thereby forming a jet of pressurized gas to force debris out of the laser cut kerf in direction 89 toward the second end 86 of generally tubular polymeric member 88. A stent pattern is cut in generally tubular polymeric member 88 near the second end 86 and the completed stent 83 is removed from the second end 86 of generally tubular polymeric member 88 leaving new second end 86' of generally tubular polymeric member 88. FIG. 8A shows the apparatus 80 before cutting of generally tubular polymeric member 88 has begun. FIG. 8B illustrates the apparatus 80 after a first stent 83 has been cut and removed. A second stent may now be cut from the remaining portion of generally tubular polymeric member 88 near new second end 86'. In one embodiment, completed stent 83 is removed by sliding completed stent 83 off of polymeric mandrel 84.

A polymeric mandrel is a mandrel made wholly or in part from at least one type of polymer or a combination of polymers, such as polymer blends or various types of copolymers. The polymeric mandrel can also be a mandrel that is coated with at least one type of polymer or a combination of polymers. The polymeric mandrel can be made from or coated with a biostable polymer or a bioerodable, biodegradable or bioabsorbable polymer. Bioerodable, biodegradable or bioabsorbable are intended to be used interchangeably unless otherwise indicated. In some embodiments, the polymer is the same as a polymer used to make the stent. In some embodiments, the polymer can be different, so long as the polymer is biocompatible.

In one embodiment, the polymeric tube and the stent made from the tube can be made entirely of a polymer or polymers. In an embodiment, the polymeric mandrel can be made entirely of a polymer or polymers.

Representative examples of biocompatible polymers that can be used for the polymeric mandrel include, but are not limited to, fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); and any derivatives, analogs, homologues, congeners, salts, copolymers and combinations thereof.

In an embodiment, the polymeric tube and stent can be made from random and block copolymers of the polymers below, in particular, poly(L-lactide-co-glycolide) (PLGA). The polymeric tube and stent can be made from PLGA including any molar ratio of L-lactide (LLA) to glycolide (GA). In particular, the polymeric tube and stent can be made from PLGA with a molar ratio of (LA:GA) including 85:15 (or a range of 82:18 to 88:12), 95:5 (or a range of 93:7 to 97:3), or commercially available PLGA products identified as having these molar ratios. Table 1 provides properties of some of the above-mentioned polymers. High strength, semicrystalline polymers with a Tg above body temperature include PLLA, PGA, and PLGA. High fracture toughness polymers include PCL, PTMC, PDO, PHB, and PBS. In some embodiments the polymeric tube and the stent are made entirely of PLLA.

TABLE 1

Properties of biodegradable polymers.

| Polymer | Glass-Transition Temp (° C.)[1] | Modulus (Gpa) | Tensile Strength (Mpa) | Elongation at break (%) | Degradation Time (months)[a] |
|---|---|---|---|---|---|
| PGA | 35-40 | 7.0[1] 5-7[2] | 60-80[2] | 30[4] | 6-12[1,2] |
| PLLA | 60-65 | 2.7[1] 3[2] | 60-70[2] | 3[4] | >24[1] >36[2] |
| PDLLA | 55-60 | 1.9[1] 2[2] | 2[2] | N/A | 12-16[1] 12-15[2] |
| PCL | (-65) – (-60) | 0.4[1,2] 0.386[4] | 20-25[2] 4[4] | 800-1000[4] | >24[1] >36[2] |
| PDO | (-10) – 0 | 1.5[1,2] | 30[2] | 35[3] | 6-12[1] 6[2] |
| PHB | N/A | 4[4] | 40[4] | 6[4] | |
| PGA-TMC | N/A | 2.4[1] | N/A | N/A | 6-12[1] |
| 85/15 PLGA | 50-55[1] | 2.0[1] | N/A | N/A | 5-6[1] |
| 75/25 PLGA | 50-55[1] | 2.0[1] | N/A | N/A | 4-5[1] |
| 65/35 PLGA | 45-50[1] | 2.0[1] | N/A | N/A | 3-4[1] |
| 50/50 PLGA | 45-50[1] | 2.0[1] | N/A | N/A | 1-2[1] |

[1]Medical Plastics and Biomaterials Magazine, March 1998.
[2]Medical Device Manufacturing & Technology 2005.
[3]The Biomedical Engineering Handbook, Joseph D. Bronzino, Ed. CRC Press in Cooperation with IEEE Press, Boca Raton, FL, 1995.
[4]Science, Vol. 297 p. 803 (2002)
[a]Degradation time also depends on part geometry.

In various embodiments, the generally tubular polymeric member, also referred to as a working tube, may be made of a different polymer or copolymer than the polymeric mandrel tube. In one embodiment, the working tube may be a pure polymer and the mandrel is a copolymer. For example, the working tube may be pure PLLA and the mandrel tube may be PLGA with a molar ratio of (LA:GA) including 85:15 or 95:5. In another example, the working tube is a pure polymer and the mandrel is a blend. For example, the mandrel tube can contain >50%, >70%, or >90% of the same polymer as the working tube. In one example, the working tube is PLLA and the mandrel tube is a blend with 60% PLLA and 40% PLGA (85:15).

Further embodiments of the invention include a working tube made of a copolymer and the mantel tube made of a copolymer. For example, both the working tube and the mandrel tube may be PLGA with a molar ratio of (LA:GA) including 85:15 or 95:5.

Utilizing the same or very similar tubing stock to make both the working tube and the mandrel tube has several advantages. First, different batches of tube stock can have different monomer and/or low molecular weight species content as contaminants, all of which can affect the degradation rate of the completed stent. Even a small amount of monomers or low molecular weight species can affect the degradation rate of a polymer. Second, if the same or similar stock is not used, new polymeric contaminants may be introduced that can affect the degradation rate of the polymer.

In some embodiments, the polymers include, but are not limited to, poly(dioxanone) and poly(ethylene oxide)/poly (lactic acid); poly(anhydrides), poly(alkylene oxalates); poly (phosphazenes); poly(urethanes); silicones; poly(esters; poly (olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; and any derivatives, analogs, homologues, congeners, salts, copolymers and combinations thereof.

In some embodiments, the polymers include, but are not limited to, poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly (ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some embodiments, at least one of polymers can be a poly(ester amide), a poly(lactide) or a poly(lactide-co-glycolide) copolymer; and any derivatives, analogs, homologues, congeners, salts, copolymers and combinations thereof.

In some embodiments, the polymers can be biodegradable, bioerodable and/or bioabsorbable. Examples of biodegradable polymers include, but are not limited to, polymers having repeating units such as, for example, an a-hydroxycarboxylic acid, a cyclic diester of an .alpha.-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, and any derivatives, analogs, homologues, congeners, salts, copolymers and combinations thereof.

In some embodiments, the biodegradable polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-co-meso-lactide), poly(D, L-lactide-co-meso-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In other embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof.

In some embodiments, the polymers are selected such that they specifically exclude any one or any combination of any of the polymers taught herein.

In the manufacturing process using device 50, 70, 80, a polymeric tube 58, 78, 88 may be placed on support member 52, 72, 82 with the polymeric mandrel 54, 74, 84 being placed inside polymer tube 58, 78, 88. The polymeric tube 58, 78, 88 may typically be between twenty to two-hundred millimeters long depending on its intended therapeutic application. Additionally, the inner and outer diameters of polymeric tube 58, 78, 88 may vary in accordance with the intended therapeutic application and in accordance with the outer diameter of mandrel 54, 74, 84. In some embodiments, the ID of polymeric tube 58, 78, 88 may approximately the same as the OD of polymeric mandrel 54, 74, 84. In one embodiment, polymer mandrels may range in size from 0.01" OD to 0.14" OD, with corresponding polymeric tubing ranging from 0.04" ID to 0.15" ID. In an embodiment, polymeric tube 58, 78, 88 is of a size between 0.07" ID and 0.13" ID, and a corresponding polymer mandrel 54, 74, 84 in the range of 0.04" OD to 0.08" OD.

In certain embodiments of the invention, if the OD of polymeric mandrel 54, 74 is too large, it may interfere with second support 51, 71. Also, if the OD of polymeric mandrel 54, 74, 84 is smaller than 0.01", then polymeric mandrel 54, 74, 84 may not provide adequate shielding during the laser cutting process. The polymeric mandrel 54, 74, 84 must be wide enough in diameter with respect to the diameter of the laser beam 100 to prevent a portion of the beam from hitting an unshielded portion of the polymeric tube 58, 78, 88. In order for polymeric mandrel 54, 74, 84 to freely roll in polymeric tube 58, 78, 88, the OD of polymeric mandrel 54, 74, 84 must be smaller than the ID of polymeric tube 58, 78, 88.

The polymeric mandrels may be solid rods with a smooth or rough outside surface. A solid rod does not contain a hollow portion between the central longitudinal axis and the outside diameter of the rod. If the rod contains a hollow portion between the central longitudinal axis and the outside diameter of the rod, it is considered a hollow rod. In another embodiment the polymeric mandrels are hollow with the outside surfaces being smooth or rough. Additionally, if polishing of the inner surface of the generally tubular polymeric member is desired, a smooth outer surface polymeric mandrel is generally preferred.

The generally tubular polymeric member from which the polymeric stent is cut is expanded, extruded tubing. The fabrication of the polymeric stent includes radially expanding an extruded polymeric tube about its cylindrical axis. Radial expansion deforms the tube circumferentially which increases the radial strength of the polymeric tubing, and the subsequently a stent fabricated from the expanded tube. The radial expansion of the polymer tube can be accomplished by a blow molding process. In such a process, the polymer tube is disposed within a cylindrical mold with a diameter greater than the polymer tube. The polymer tube is heated. The pressure inside of the tube is increased by blowing a gas into the tube to cause radial expansion of the tube so the outside surface of the tube conforms to the inside surface of the mold. The polymer tube can be axially deformed by a tensile force along the tube axis before, during, and/or after the radial deformation. In some instances, only sufficient tension is applied to maintain the length of the tube as it is expanded. The polymer tube is then cooled below Tg and further processing steps can then be performed, such as laser machining of the tube to form a stent pattern.

The polymeric mandrel may be made from the same stock tubing as the generally tubular polymeric member by expanding each tube to a different diameter. In an embodiment, the polymeric mandrel is expanded to a smaller diameter than the generally tubular polymeric member.

A laser 100 may be used for the etching process when forming a polymeric stent 10 from polymeric tube 8 in FIG. 1. The laser 100 may be used in a range of fifty milliwatts to one watt, depending on the environmental conditions surrounding the laser. A typical lasing process to complete an entire stent takes approximately two minutes to twelve minutes, more particularly approximately six minutes, pursuant to a method of this invention.

Figure 8D:
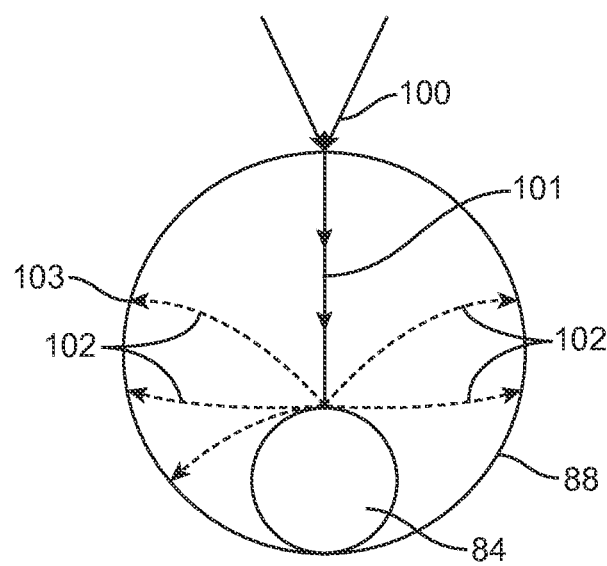
FIG. 8D illustrates an end view of an embodiment of the device in FIGS. 8A, 8B.

One of skill in the art will realize that the strength of the laser and the thickness of the polymeric mandrel should be adjusted so that the laser cuts through the polymeric tube and either degrades the surface of the polymeric mandrel or cuts through the mandrel if it is hollow. In one embodiment, the polymeric mandrel is hollow of a thickness that allows the laser to penetrate one side of the polymeric mandrel, without going entirely through the polymeric mandrel. Polymeric mandrels with thinner walls are preferred because they are lighter and are preferentially worn away by the laser before the polymeric tube. As shown in FIG. 8D, if a solid polymeric mandrel 84 is used, or the walls are too thick on the polymeric mandrel 84, the laser beam 101 from laser 100 may scatter material as well as energy 102 instead of absorbing the energy, possibly resulting in damage 103 to the inner surface of polymeric tube 88.

In FIG. 9, a polymeric stent 10 manufactured in accordance with device 50, 70, 80 is illustrated. As discussed previously, the polymeric stent 10 can include a plurality of struts 12 linked by connecting elements 14, with gaps 16 positioned between the struts and the connecting elements. The polymeric stent 10 can also include a proximal ring 18, a distal ring 20 and at least one central ring 22. Generally, the polymeric stent 10 is a bioerodable, biodegradable or bioabsorbable implantable medical device that is intended to remain in the body until its intended function is achieved.

In FIGS. 10 and 11, cross-sectional and enlarged views of the polymer stent of FIG. 9 are illustrated, respectively. Generally absent from the inner surface 26 is at least one angled cut 28. This is substantially due to the polymeric mandrel 54, 74, 84, which provides a shielding effect to the inner surface when the equal-but-opposite outer surface is being lased during the manufacturing process. Moreover, because polymeric mandrel 54, 74, 84 is composed of a biocompatible polymer, the problems of undesirable residual contaminants left by typical glass or metal mandrels, for example, are substantially reduced or completely eliminated. In one embodiment, the working polymeric tube is substantially free of metal and glass. In an embodiment the polymeric mandrel is substantially free of metal and glass.

In a further embodiment, the mandrel may be designed to absorb any laser light that leaks through from the cutting process. The mandrel may be manufactured by adding a pigment or a dye to the polymeric material during the extrusion process, or by placing a second mandrel inside of the hollow polymer mandrel. In an embodiments, the second mandrel is constructed of a metallic material, or a material that can strongly absorb light. This would assist in preventing the scattering of light illustrated in FIG. 8D.

The polymeric stent 10 described in FIGS. 9, 10 and 11 may be coated with one or more therapeutic agents, including an anti-proliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof.

The coating method may be applied by a variety of methods, such as those disclosed in U.S. Pat. No. 6,818,063 to Kerrigan and U.S. Pat. No. 6,695,920 to Pacetti et al. In addition, the therapeutic drug may be incorporated within the polymeric tube 8 thereof, such as disclosed in U.S. Pat. No. 5,605,696 to Eury et al. Also, the polymeric tube 8 may include at least two layers of polymers with different chemical characteristics for purposes of, for example, adjusting the flexibility characteristic of the polymeric stent 10.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of producing a polymeric stent, the method comprising:
    positioning a polymeric mandrel and polymeric tube relative to one another such that the polymeric mandrel is within the polymeric tube and in contact with the polymeric tube inside surface, thereby forming a tubing-mandrel assembly,
    wherein the polymeric tube has a first end and a second end;
    cutting the polymeric tube while the polymeric mandrel is positioned within the polymeric tube with a laser to form a stent,
    wherein during the cutting the polymeric tube rotates and the polymeric mandrel rolls on the inside surface of the polymeric tube in response to an angular force from the rotation of the polymeric tube, and
    wherein there are imperfections including bumps on the inside surface of the polymeric tube or on an outer surface of the polymeric mandrel contacting the polymeric tube which cause the polymeric mandrel to have a bouncy, irregular, motion during the rolling; and
    removing the stent from the mandrel.

2. The method of claim 1, wherein the polymeric tube is only supported at the first end during the cutting.

3. The method of claim 1, wherein the polymeric tube is supported at the first end and the second end during the cutting.

4. The method of claim 1, further comprising dispensing pressurized gas through a nozzle near the laser cutting, thereby forming a jet of pressurized gas to force cut debris toward the second end of the polymeric tube.

5. The method of claim 4, wherein the nozzle dispenses the pressurized gas at an angle between 0 and 90 degrees relative to a working outer tube surface.

6. The method of claim 4, wherein the gas is an inert gas.

7. The method of claim 4, wherein the gas temperature is less than ambient temperature.

8. The method of claim 1, wherein the polymeric mandrel is hollow.

9. The method of claim 1, wherein the polymeric mandrel is a solid rod that is not hollow.

10. The method of claim 1, wherein the polymeric mandrel is moved longitudinally along the inside surface of the polymeric tube toward the first or second end.

11. The method of claim 1, wherein the polymeric tube and the polymeric mandrel are formed from at least one of poly (L-lactide) and poly(L-lactide-co-glycolide).

12. The method of claim 1, wherein the polymeric tube and the polymeric mandrel are formed from the same bioerodable polymer.

13. A method of producing a polymeric stent, the method comprising:
    positioning a polymeric mandrel and polymeric tube relative to one another such that the polymeric mandrel is within the polymeric tube and in contact with the polymeric tube inside surface, thereby forming a tubing-mandrel assembly,
    wherein the polymeric tube has a first end and a second end;
    cutting the polymeric tube while the polymeric mandrel is positioned within the polymeric tube with a laser to form a stent,
    wherein during the cutting the polymeric tube rotates and the polymeric mandrel rolls on the inside surface of the polymeric tube in response to an angular force from the rotation of the polymeric tube, and
    wherein an outer surface of the polymeric mandrel contacting the polymeric tube is roughened and the inside surface of the polymeric tube is polished by the roughened surface of the polymeric mandrel during the rolling; and
    removing the stent from the mandrel.

* * * * *